United States Patent
Cooper

(10) Patent No.: US 10,442,036 B2
(45) Date of Patent: Oct. 15, 2019

(54) TEST PLATE FOR APPROVING STEEL OR METAL WELDING PARAMETERS: METHOD OF APPROVING STEEL AND METAL WELDING PARAMETERS: UNDER MATCHED BUTT WELDED PLATES

(71) Applicant: BAE SYSTEMS plc, London (GB)

(72) Inventor: Norman Cooper, Cumbria (GB)

(73) Assignee: BAE SYSTEMS PLC, London (GB)

( * ) Notice: Subject to any disclaimer, the term of this patent is extended or adjusted under 35 U.S.C. 154(b) by 405 days.

(21) Appl. No.: 15/319,482

(22) PCT Filed: Jun. 16, 2015

(86) PCT No.: PCT/GB2015/051755
§ 371 (c)(1),
(2) Date: Dec. 16, 2016

(87) PCT Pub. No.: WO2015/193650
PCT Pub. Date: Dec. 23, 2015

(65) Prior Publication Data
US 2017/0129055 A1     May 11, 2017

(30) Foreign Application Priority Data
Jun. 18, 2014   (GB) .................................. 1410872.4

(51) Int. Cl.
*G01N 33/00*    (2006.01)
*B23K 33/00*    (2006.01)
*B23K 31/02*    (2006.01)
*B23K 31/12*    (2006.01)
(Continued)

(52) U.S. Cl.
CPC .............. *B23K 33/00* (2013.01); *B23K 31/02* (2013.01); *B23K 31/125* (2013.01); *G01N 33/20* (2013.01); *B23K 2103/04* (2018.08)

(58) Field of Classification Search
CPC .......................... B23K 31/125; B23K 2103/04
See application file for complete search history.

(56) References Cited

U.S. PATENT DOCUMENTS

2009/0077758 A1\* 3/2009 Vincent ................. E01D 19/125
14/73

OTHER PUBLICATIONS

Computer english translation KR20110120527 (Year: 2011).\*
(Continued)

*Primary Examiner* — Erin B Saad
(74) *Attorney, Agent, or Firm* — Finch & Maloney PLLC

(57) ABSTRACT

A test method is provided to reproducibly test under matched HY100 welds to robustly establish the production parameters for the welding process. The test method comprises forming a 'U' shaped groove in a plate to which steel members are welded on the reverse side. The steel members comprise transverse members that extend across the weld. The transverse members are arranged at a density of at least four members for each 0.5 m length of weld and preferably five transverse members. The steel members further comprise longitudinal stiffeners that extend parallel to the weld. The longitudinal stiffeners are arranged at a density of two stiffeners per 0.4 m width of the plate. The high density of stiffeners has provided a reproducible and reliable weld test method that is capable of being used to establish and approve production parameters for the welding process of under matched HY100 welds.

20 Claims, 2 Drawing Sheets

(51) Int. Cl.
*G01N 33/20* (2019.01)
*B23K 103/04* (2006.01)

(56) References Cited

OTHER PUBLICATIONS

Steel Grades https://www.steel-grades.com/Steel-Grades/Carbon-Steel/18/6413/_HY-100.pdf from way-back.com Feb. 7, 2014 (Year: 2014).*
International Preliminary Report on Patentability received for Patent Application No. PCT/GB2015/051755, dated Dec. 29, 2016. 8 pages.

* cited by examiner

TEST PLATE FOR APPROVING STEEL OR METAL WELDING PARAMETERS: METHOD OF APPROVING STEEL AND METAL WELDING PARAMETERS: UNDER MATCHED BUTT WELDED PLATES

The present invention relates to a method of welding High Yield (HY) Strength Steels and a method of testing the welding procedures for acceptance against standards. In particular, the invention is concerned with the welding of HY100 steel.

To achieve a commercially acceptable welding procedure, the welding parameters such as weld consumable material, preheat temperatures, inter pass temperatures and post heating temperatures need to be approved against accepted standards. Welding parameters are approved for a refined HY80 named Q1(N) which has good through-thickness properties, is resistant to tearing, and has a minimum proof stress of 550 MPa. Where weld failure could be catastrophic the standards dictate that the yield strength of the weld material match or exceed that of the parent plate, which is termed an over-matched weld. This is done primarily to protect the weld from localization of plastic strain in the event that the yield load of the structure is exceeded, i.e. to force the plastic deformation to occur primarily in the parent plate.

The push for stronger, lighter structures necessitates the welding of HY100 steels. As mentioned, to avoid plastic strain, the accepted practice when weld failure could be catastrophic is to use over-matched weld material. Whilst over-matched HY100 welds may initially produce acceptable welds, because pre-heating to 120° C. is normally required, the welds have increased susceptibility to hydrogen assisted cracking (HAC) in the weld and heat affected zone (HAZ). This form of cracking, when it occurs, can be either intergranular, transgranular or both intergranular and transgranular relative to prior austenite grains. This form of cracking may also be termed Delayed Cracking, since cracking occurs after the welding has been completed and cooled down, with instances of cracking documented as only being found a number of months after the welding operation was completed. The most common form of Hydrogen cracking occurs in the Heat Affected Zones (HAZ) of a weld; however when high strength weld metal is utilised, Hydrogen cracking can also occur in the weld metal itself. Although it is accepted that Hydrogen must be present during the welding operation, the exact mechanism by which Hydrogen crack formation occurs is not fully understood, and it is considered that a number of mechanisms may play a role in any one instance. However, it is generally regarded that the four factors necessary to produce HAC are: a susceptible microstructure; the level of diffusible hydrogen in the weld metal and/or HAZ; the presence of tensile residual stresses; and a susceptible temperature band.

Prevention of HAC in over-matched HY100 welding processes is usually achieved by the restriction of hydrogen during the welding process. However, the high pre-heat temperatures have implications on the cost of energy, extended lead times for structures to reach the higher temperature before welding can commence and the unfavourable working conditions having a knock on effect on productivity.

It is an object of the present invention to overcome at least one of the above or other disadvantages. It is a further aim to provide a weld procedure having reduced cost. A further aim is to provide a test procedure suitable for qualifying weld procedures and in particular to a test procedure that is reproducible.

According to the present invention there is provided a method of welding, for example, HY100 steel and a method of testing welds as set forth in the appended claims. Other features of the invention will be apparent from the dependent claims, and the description which follows.

A method of welding HY100 is provided. The method uses under matched weld consumables having a lower tensile strength compared to the parent metal. The weld procedure uses a 70° C. preheat minimum. The method comprises bring together two pieces of parent material to be welded together. The parent material is preheated. The method comprises heating the weld consumable to join the two pieces of parent material. Because the weld metal is weaker than the parent metal, as the weld metal cools down, the shrinkage contraction will be accommodated by the weld metal plastically deforming. The plastic deformation of the weld metal during this cooling down period will therefore shield the HAZ material from the applied contraction stresses, thereby reducing the likelihood of hydrogen cracking in the HAZ.

Advantageously, the lower pre-heat temperature has implications on the cost of energy, lead times for structures to reach temperature before welding can start and the temperature of the working conditions which has a knock on effect on productivity. It is thought that the result will be a significant reduction in welding costs.

In the exemplary embodiments, the inter pass temperature is a maximum 150° C., which is consistent with current welding standards for Q1(N) welds.

In the exemplary embodiments, the maximum flux cored consumable shelf life is 3 days after opening the vacuum packaging, which is consistent with current welding standards for Q1(N) welds.

In the exemplary embodiments, a minimum 24 hour delay time from completion and cool down of the weld was able to be specified, which is consistent with current welding standards for Q1(N) welds.

Advantageously, maintaining the welding standards for HY100 under matched welds to be consistent with current standards for Q1(N) welds allows costs savings to be made through the manufacturing processes and when moving from Q1(N) matched welds to HY100 under matched welds. It has been further found that using the same weld consumable for Q1(N) matched welds as the weld material for under matched HY100 welds increases these advantages.

A test method is also provided to reproducibly test welds to robustly establish the production parameters for the welding process. The test method comprises forming a 'U' shaped groove in a 0.05 m thick plate to which steel members are welded on the reverse side. The steel members comprise transverse members that extend across the weld. The transverse members are arranged at a density of at least four members for each 0.5 m length of weld and preferably five transverse members. The steel members further comprise longitudinal stiffeners that extend parallel to the weld. The longitudinal stiffeners are arranged at a density of two stiffeners per 0.4 m width of the plate. Whilst this density of stiffeners represents a higher level of restraint condition than would be experienced in use, a lower density of stiffening has not reproduced cracking even in sample welding conditions known to produce cracking. In contrast, the increased density of stiffeners has provided a reproducible and reliable weld test method that is capable of being used to establish and approve production parameters for the welding process of under matched HY100 welds.

The test method comprises completing a weld under the production parameters being approved to fill the 'U' shaped groove so that the full section consists of sound metal. Following welding, the weld caps are dressed flushed and mechanised Time of Flight Diffraction (ToFD) undertaken at time intervals of nominally 24 hours, 48 hours, 72 hours, 7 days and 14 days. Metallurgical examination of each weld is undertaken to examine for cracks and to approve the welding conditions.

Advantageously, the test method provides a reproducible weld test for robustly establishing welding parameters for under matched HY100 welds. Although currently it is not necessarily required to undertake non-destructive Examination (NDE) of welds for transverse weld metal cracking when approving welding parameters, it is required for confidence in the under matched HY100 welding parameters due to the increased susceptibility to transverse weld cracking brought about by HAC and the concentration effect of long range longitudinal stresses. The test method therefore provides a test method for approving HY100 welding parameters. Although single run weld test such as TEKKEN are available, these are dominated by the tri-axial stress regime in the root region. Whilst this reflects a highly restrained fillet weld, it does not represent the conditions of a multi-pass butt weld and as such the results of this type of test would lead to approval of more conservative welding parameters. For instance, the pre-heat temperatures would be approved at much higher temperatures.

The inventive principles might more broadly be described/defined as a test plate for approving steel or metal welding parameters using an under matched weld consumable, the test plate comprising a plate of steel or metal having a groove machined along a length of the plate, wherein transverse stiffening members are welded to a rear of the plate; and the transverse stiffening members having a density parallel to the weld of more than two members for each 0.5 m of weld.

The members might further comprise longitudinal stiffeners that extend parallel to the weld. The longitudinal stiffeners might be arranged at a density of two stiffeners per 0.4 m width of the plate.

The invention might find particular use with HY100 steel.

In a related manner, a method of approving steel or metal welding parameters using an under matched weld consumable is provided, the method comprising using a test plate as described above, depositing a weld in the groove using the weld parameters to be approved, and conducting NDE testing of the formed weld using ToFD.

In a related manner, an under matched butt weld joining two plates of steel or metal is provided, wherein the weld has been formed following welding parameters approved using the method as described above.

Features of different embodiments can be combined and/or replace one another, unless such combination/replacement would be considered to be incompatible by the skilled person from a reading and understanding of this disclosure.

For a better understanding of the invention, and to show how embodiments of the same may be carried into effect, reference will now be made, by way of example, to the accompanying diagrammatic drawings in which.

Figure 1:
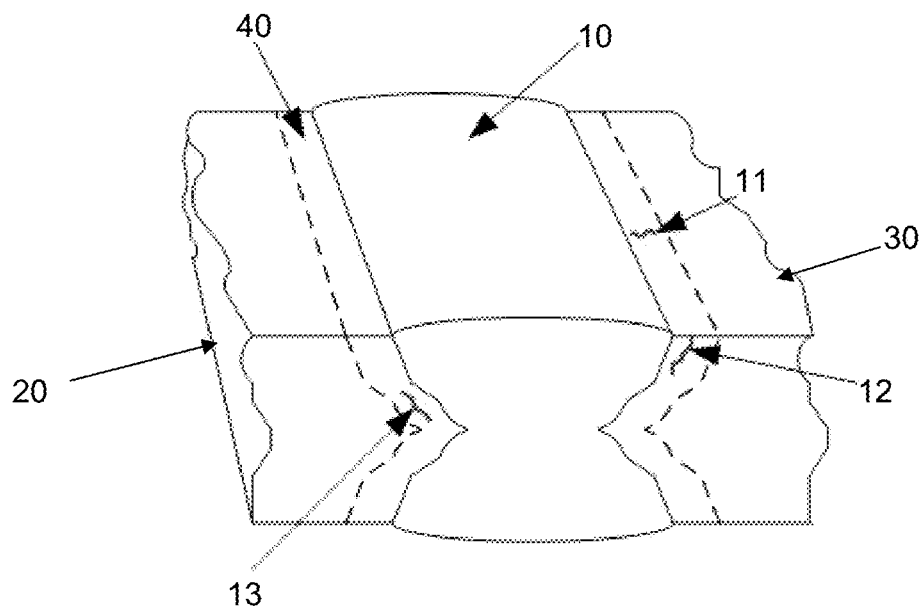
FIG. 1 is a schematic representation of a but weld showing typical HAC.

FIG. 1 is a schematic representation of the positions where Hydrogen Assisted Cracking can occur in a butt weld. The butt weld 10 is formed between first 20 and second 30 pieces of HY100 steel. The weld consumable is under matched to the HY100 steel. That is the yield strength of the weld consumable is lower than HY100 steel. In the Heat affected zone (HAZ) 40, if the welding parameters used to create the weld are inadequate or not tightly enough controlled, transverse cracks 11, toe cracks 12, and underbead cracks 13 can form after a number of months after the welding operation is completed. It is therefore necessary to destructively test sample welds created using controlled welding parameters representative of the parameters intended for use in the manufacturing environment so that the weld parameters can be approved. In addition to the current destructive testing of sample welds to verify welding parameters, it is necessary to test and approve the sample welds in relation to Hydrogen Assisted Cracking (HAC).

Figure 2:
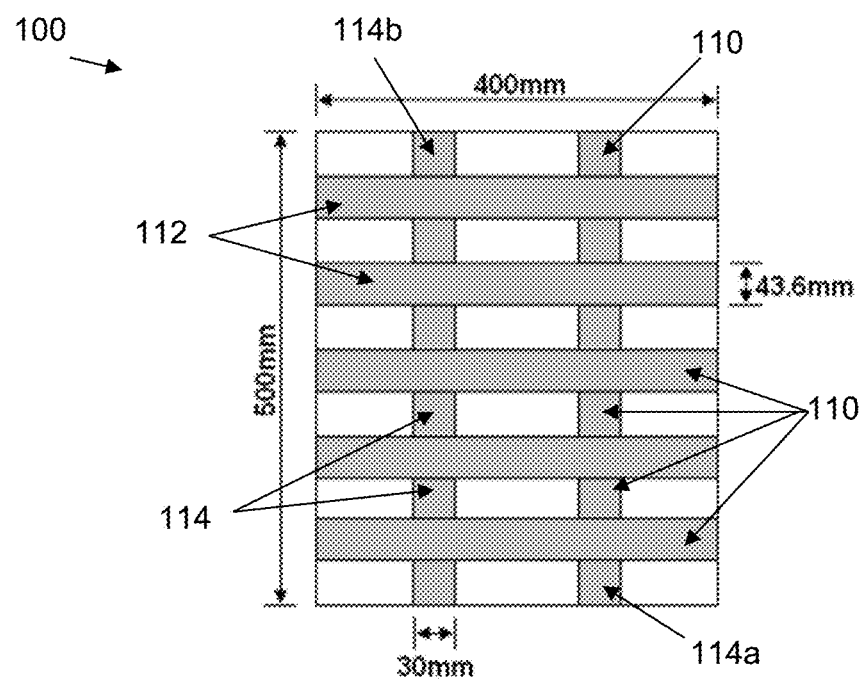
FIG. 2 is a rear view of a test piece.
Figure 3:
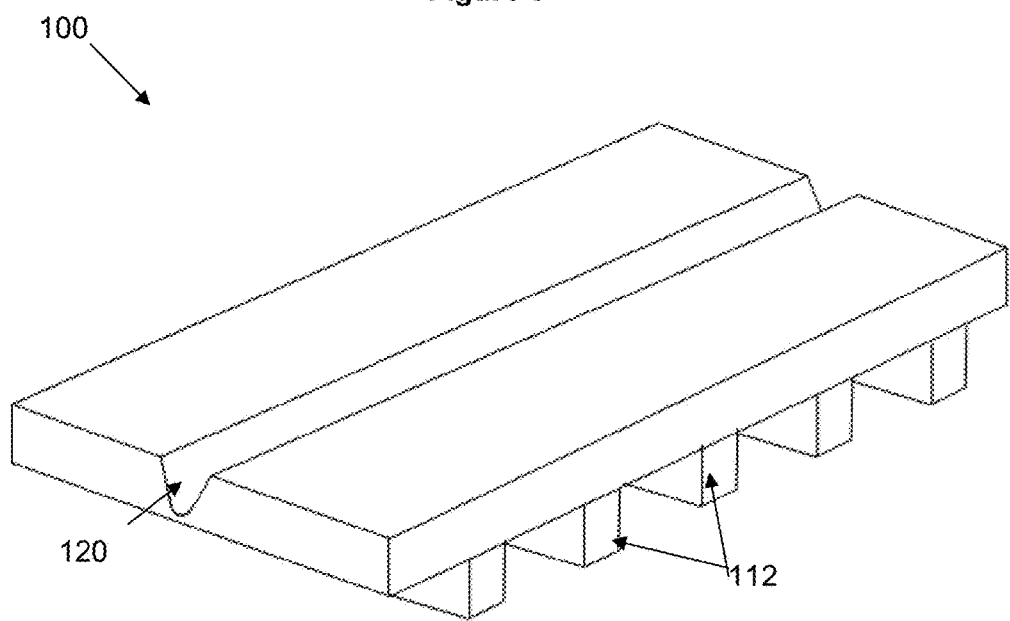
FIG. 3 is a perspective view of the test piece.
Figure 4:
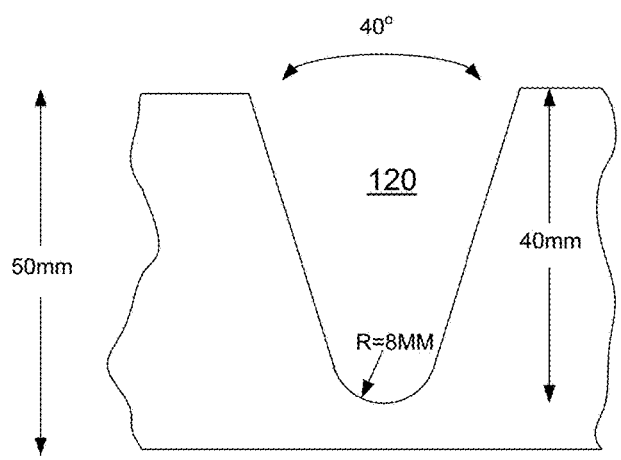
FIG. 4 is an end view of a portion of the test piece.

Referring to FIGS. 2 to 4, welding parameters for HY100 butt welds are approved using a test plate 100. The test plate 100 is a 0.05 m plate of HY100 steel. As shown in FIG. 2, the plate has a width of 0.4 m transverse to the weld and a length parallel to the weld of 0.5 m. Stiffeners 110 are welded to the rear of the plate 100. The stiffeners 110 restrain the plate 100 to stimulate cracking during NDE of the butt weld through ToFD as is known in the art. The stiffeners 110 are steel members comprising transverse stiffeners 112 and longitudinal stiffeners 114.

As shown in FIG. 2, the transverse stiffeners 112 are heavy transverse stiffeners having a width of between 7% to 10% of the length of the plate 100, or 8% to 9% of the length of the plate 100. The width of the transverse stiffeners 112 is shown in FIG. 2 as being 0.0436 m. The density of the transverse stiffeners 112 is high. As further shown in FIG. 2, the transverse stiffeners 112 are evenly pitched across the length of the plate 100. Suitably, the density is at least four transverse stiffeners 112 for each 0.5 m of plate length. In the figures five transverse stiffeners 112 are shown. Here a stiffener is provided for each 0.1 m of plate length. The transverse stiffeners 112 are welded across the rear of the plate 100, transverse the weld and so as to extend substantially the full width of the plate 100.

Longitudinal stiffeners 114 are welded between the transverse stiffeners 112. The longitudinal stiffeners 114 have a width of between 6% to 9%, or 7% to 8% of the width of the plate 100. In FIG. 2, the longitudinal stiffeners 114 are shown having a width of 0.03 m. The longitudinal stiffeners 114 are welded to the plate 100 and transverse stiffeners 112 in a line along the length of the plate 100. End sections 114a and 114b of the longitudinal stiffeners 114 that do not extend between two transverse stiffeners 112 are optional. The longitudinal stiffeners 114 are formed in lines along the length of the plate 100 to form longitudinal stiffener groups. The density of the longitudinal stiffener groups is shown as being two stiffeners for each 0.4 m of plate width, though the density may be as high as two stiffeners for each 0.3 m of plate width. In FIG. 2, the longitudinal stiffeners 114 are shown in two longitudinal stiffener groups spaced equally either side of the weld.

As can be seen in the perspective view of FIG. 3, the front of the plate 100 a 'u' shaped groove 120 is machined along a centre of the plate. The groove 120 has a depth at least 60% or at least 70% of the thickness of the plate 100. In FIG. 4, the groove 120 is shown having a depth of 80% of the thickness of the plate. The bevel angle of each side of the groove 120 is 15-25°, and is shown as 20° in FIG. 4. The bottom of the groove 120 is radiused at around 20% of the depth of the groove 120. The test weld is deposited in the groove 120 in a series of passes as is known in the art and using the weld parameters to be approved. The formed weld caps are dressed and flushed. NDE such as a mechanised ToFD is undertaken at time intervals of nominally 24 hours, 48 hours, 72 hours, 7 days and 14 days. Following completion of the NDE cycle metallurgical examination of each panel was undertaken, concentrating on any areas where features were identified by ToFD, and consisting of transverse weld macros, longitudinal macros through weld centerline, and micro sections. Any features of interest are then subjected to further in depth analysis. Consequently, a test method is provided to robustly establish and approve the production parameters for welding HY100 under matched welds.

Using the test plate as described herein, weld parameters for HY100 under matched welds were able to be established. The welding parameters used a preheat temperature of less than 90° C. or less than 80° C. and preferably around 70° C. A maximum inter pass temperature of 165° C. or 160° C. and preferably around 150° C. was used. These temperatures are considerably lower than could have been approved using existing test techniques.

Although preferred embodiment(s) of the present invention have been shown and described, it will be appreciated by those skilled in the art that changes may be made without departing from the scope of the invention as defined in the claims.

For instance, the plate described may be used with or formed from other materials than HY100 steel. Other metals/steels may be used. The described principles may be advantageous for such other materials.

Additionally, the use of transverse stiffening members as described above may be advantageous without the use of longitudinal stiffening members. The use of longitudinal stiffening members may be optional, but may add to the advantageous nature of the test.

Transverse stiffening members having a density parallel to the weld of more than (only) two members for each 0.5 m of weld may be advantageous. Three of more may be even more advantageous, and four or more even more so. Five may be particularly advantageous.

The invention claimed is:

1. A test plate for approving HY100 welding parameters using an under matched weld consumable compared to HY100 steel, the test plate comprising:
   a plate of HY100 steel having a groove machined along a length of a front of the plate and through only a portion of a thickness of the plate;
   a plurality of transverse stiffening members welded to a rear of the plate and extending across the groove; and
   a plurality of longitudinal stiffening members welded to the rear of the plate and extending parallel to the groove.

2. The test plate of claim 1, wherein a density of the transverse stiffening members is five members for each 0.5 m of groove.

3. The test plate of claim 1, wherein the longitudinal stiffening members have a density of two members for each 0.4 m of plate width.

4. The test plate of claim 1, wherein each transverse stiffening member extends a width of the plate and transverse the groove.

5. The test plate of claim 1, wherein each transverse stiffening member has a width relative to the length of the plate in a direction of the groove of between 7% to 10%.

6. The test plate of claim 1, wherein the longitudinal stiffening members are formed into longitudinal stiffening groups, wherein the longitudinal stiffening members of each group are aligned along a common plane that runs parallel to the groove.

7. The test plate of claim 6, wherein the longitudinal stiffening members of each group extend between the transverse stiffening members.

8. The test plate of claim 1, wherein the longitudinal stiffening members have a width relative to a width of the plate transverse the groove of between 6% to 9%.

9. The test plate of claim 8, wherein the relative width is between 7% and 8% of the width of the plate.

10. The test plate of claim 1, wherein the plate has a width across the groove of 0.4 m and a length along the groove of 0.5 m.

11. A method of approving HY100 welding parameters using an under matched weld consumable, the method comprising:
    using the test plate of claim 1, depositing a weld in the groove using the weld parameters to be approved, and conducting non-destructive examination (NDE) testing of the formed weld using time of flight diffraction (ToFD).

12. An under matched butt weld joining two plates of HY100 steel, wherein the weld has been formed following welding parameters approved using the method of claim 11.

13. The under matched butt weld of claim 12, wherein the weld is formed using a minimum preheat of less than 90° C.

14. A test plate for approving steel or metal welding parameters using an under matched weld consumable compared to the test plate material, the test plate comprising:
    a plate of steel or metal having a groove machined along a length of a front of the plate and through only a portion of a thickness of the plate, wherein transverse and longitudinal stiffening members are welded to a rear of the plate; and
    the transverse stiffening members having a density in a direction parallel to a direction of the length, the transverse stiffening member density being more than three members for each 0.5 m of the length; and
    the longitudinal stiffening members having a density in a direction perpendicular to the direction of the length, the longitudinal stiffening member density being at least two members for each 0.4 m of plate width.

15. A method of approving steel or metal welding parameters using an under matched weld consumable, the method comprising using the test plate of claim 14, depositing a weld in the groove using the weld parameters to be approved, and conducting non-destructive examination (NDE) testing of the formed weld using time of flight diffraction (ToFD).

16. The test plate of claim 1, wherein a density of the transverse stiffening members is at least four members for each 0.5 m of groove.

17. The test plate of claim 1, wherein the longitudinal stiffening members have a density of two members for each 0.3 m of plate width.

18. The test plate of claim 14, wherein the transverse stiffening member density is four members for each 0.5 m of the length.

19. The test plate of claim 14, wherein the transverse stiffening member density is five members for each 0.5 m of the length.

20. The test plate of claim 14, wherein the longitudinal stiffening member density is at least two members for each 0.3 m of plate width.

\* \* \* \* \*